US010314526B2

(12) United States Patent
Shimuta et al.

(10) Patent No.: US 10,314,526 B2
(45) Date of Patent: *Jun. 11, 2019

(54) BIOSENSOR

(71) Applicant: Murata Manufacturing Co., Ltd., Nagaokakyo-shi, Kyoto-fu (JP)

(72) Inventors: Toru Shimuta, Nagaokakyo (JP); Yasutaka Fujii, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 348 days.

This patent is subject to a terminal disclaimer.

(21) Appl. No.: 15/421,537

(22) Filed: Feb. 1, 2017

(65) Prior Publication Data

US 2018/0008177 A1    Jan. 11, 2018

Related U.S. Application Data

(63) Continuation of application No. 14/183,069, filed on Feb. 18, 2014, now Pat. No. 9,592,000, which is a
(Continued)

(30) Foreign Application Priority Data

Aug. 19, 2011    (JP) ................. 2011-179987

(51) Int. Cl.
*A61B 5/1455*    (2006.01)
*A61B 5/00*    (2006.01)
*A61B 5/0245*    (2006.01)

(52) U.S. Cl.
CPC ........ *A61B 5/14552* (2013.01); *A61B 5/0245* (2013.01); *A61B 5/688* (2013.01);
(Continued)

(58) Field of Classification Search
CPC . A61B 5/1455; A61B 5/0205; A61B 5/14551; A61B 5/14552; A61B 5/14532; A61B 5/0245

See application file for complete search history.

(56) References Cited

U.S. PATENT DOCUMENTS 4,880,304 A * 11/1989 Jaeb .................. A61B 5/14552
356/41
5,413,690 A    5/1995 Kost et al.
(Continued)

FOREIGN PATENT DOCUMENTS

CN    201290680 Y    8/2009
CN    201668391 U    12/2010
(Continued)

OTHER PUBLICATIONS

Japanese Patent Office (Notice of Reasons for Revocation of Granted counterpart JP Patent following Written Opposition dated Sep. 30, 2015), dispatch date of Notice Jan. 8, 2016 (with English translation).
(Continued)

*Primary Examiner* — Eric F Winakur
*Assistant Examiner* — Chu Chuan Liu
(74) *Attorney, Agent, or Firm* — Arent Fox LLP

(57) ABSTRACT

A biosensor including light emitting elements and a light receiving element disposed on a principal surface of a wiring board; a light shielding portion disposed between a light-emitting-element sealing portion and a light-receiving-element sealing portion; a base medium having light transmitting properties, disposed in parallel with the wiring board with the light shielding portion therebetween; an adhesion layer having light transmitting properties that bonds the base medium with the light-emitting-element sealing portion, the light-receiving-element sealing portion, and the light shielding portion; and a first electrocardiograph electrode attached
(Continued)

to a principal surface of the base medium. Both end portions of the adhesion layer and both end portions of the base medium are disposed such that they overlap neither of the light-receiving-element sealing portion nor the light-emitting-element sealing portion when viewed from a direction normal to the principal surface of the wiring board.

20 Claims, 6 Drawing Sheets

Related U.S. Application Data continuation of application No. PCT/JP2012/005065, filed on Aug. 9, 2012.

(52) U.S. Cl.
CPC ............... *A61B 2562/0209* (2013.01); *A61B 2562/0233* (2013.01); *A61B 2562/16* (2013.01)

(56) References Cited

U.S. PATENT DOCUMENTS

| | | | |
|---|---|---|---|
| 5,584,296 A * | 12/1996 | Cui ................... | A61B 5/14552 356/41 |
| 7,026,654 B2 * | 4/2006 | Igaki ................ | H01L 31/02325 257/13 |
| 8,599,170 B2 | 12/2013 | Takakura | |
| 2008/0049565 A1 | 2/2008 | Ishida et al. | |
| 2008/0146906 A1 | 6/2008 | Baker et al. | |
| 2008/0219673 A1 * | 9/2008 | Goh .................... | H04B 10/40 398/135 |
| 2009/0156912 A1 * | 6/2009 | Kuhn .................. | A61B 5/0086 600/310 |
| 2009/0182208 A1 | 7/2009 | Cho et al. | |
| 2009/0202251 A1 | 8/2009 | Shibayama | |
| 2010/0056887 A1 | 3/2010 | Kimura et al. | |
| 2011/0009719 A1 | 1/2011 | Al-Ali et al. | |
| 2011/0092832 A1 | 4/2011 | Onoe et al. | |
| 2011/0254108 A1 | 10/2011 | Gozzini et al. | |
| 2011/0260176 A1 | 10/2011 | Onoe et al. | |
| 2012/0071734 A1 | 3/2012 | Shimuta et al. | |

FOREIGN PATENT DOCUMENTS

| | | |
|---|---|---|
| CN | 201912089 U | 8/2011 |
| EP | 1 810 613 A1 | 7/2007 |
| EP | 2087837 A1 | 8/2009 |
| EP | 2 277 440 A1 | 1/2011 |
| EP | 2425768 A1 | 3/2012 |
| JP | H02-21844 A | 1/1990 |
| JP | H06029504 U | 2/1994 |
| JP | 2000075155 A | 3/2000 |
| JP | 2002072021 A | 3/2002 |
| JP | 2005315818 A | 11/2005 |
| JP | 2006158974 A | 6/2006 |
| JP | 200813113 A | 8/2008 |
| JP | 2011-049473 A | 3/2011 |
| JP | 2011-70383 A | 4/2011 |
| JP | 2013-000378 A | 1/2013 |
| WO | WO 2007097240 A1 | 8/2007 |
| WO | WO 2008065699 A1 | 6/2008 |
| WO | WO 2009019836 A2 | 2/2009 |
| WO | WO 2009/139029 A1 | 11/2009 |
| WO | WO 2009139028 A | 11/2009 |
| WO | WO 2010125705 A1 | 11/2010 |

OTHER PUBLICATIONS

Written Opinion and International Search Report issued in PCT/JP2012/005065 dated Oct. 2, 2012.

* cited by examiner

BIOSENSOR

CROSS REFERENCE TO RELATED APPLICATIONS

The present application is a continuation of U.S. application Ser. No. 14/183,069, filed Feb. 18, 2014, which is a continuation of PCT/JP2012/005065 filed Aug. 9, 2012, which claims priority to Japanese Patent Application No. 2011-179987, filed Aug. 19, 2011, the entire contents of each of which are incorporated herein by reference.

TECHNICAL FIELD OF THE INVENTION

The present invention relates to a biosensor which obtains biological signals.

BACKGROUND OF THE INVENTION

These days, people are more and more concerned about health care and health maintenance and promotion. It is thus desirable that people can more easily obtain biological information, such as the pulse and electrocardiograms. Pulse monitors or pulse oximeters are known. More specifically, in such devices, by utilizing characteristics in which hemoglobin within the blood absorbs light in a range from visible light to infrared light, a change in the intensity of light passing through or reflected by a body, such as a finger, is obtained as a photoplethysmographic signal.

Patent Document 1 discloses a biological information monitoring sensor which serves both as a body electrode and an oximeter probe. By using this biological information monitoring sensor, taking of an electrocardiogram and measuring of oxygen saturation of hemoglobin within the blood can be performed simultaneously. More specifically, this biological information monitoring sensor includes an electrode element attached on a polymer film, an LED, which serves as a light emitting element, and a PD, which serves as a light receiving element, fixed on the electrode element with a predetermined spacing between the LED and the PD, and AMPS, which serves as a transparent conductive gel, for covering the elements. With this configuration, when the sensor contacts the skin surface of a body, the electrode element is brought into contact with the skin via the conductive AMPS, and thus, the function as a normal electrode element can be obtained. Meanwhile, the LED and the PD are in contact with the skin via the transparent AMPS, and thus, the function as an oximeter probe can be obtained.

Patent Document 1: Japanese Unexamined Utility Model Registration Application Publication No. 6-29504

As stated above, in the biological information monitoring sensor disclosed in Patent Document 1, the light emitting element (LED) and the light receiving element (PD) are covered with the transparent conductive gel (AMPS), and the LED and the PD contact a body skin via the transparent AMPS. Accordingly, when monitoring is performed, part of light emitted from the LED (detection light) may directly reach the PD via the transparent AMPS. Normally, the intensity of light (stray light) emitted from the LED and reaching the PD without passing through or being reflected by a body is higher than the intensity of light passing through or being reflected by a body. Thus, light to be detected, that is, light passing through or being reflected by a body, is embedded in stray light (noise), which may decrease the S/N ratio.

SUMMARY OF THE INVENTION

The present invention has been made in order to solve the above-described problem. It is an object of the present invention to provide a biosensor which obtains photoplethysmographic signals and which is capable of reducing the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion; and a plane electrode attached to a principal surface of the base medium such that the plane electrode overlaps neither of the light emitting element nor the light receiving element when viewed from a direction normal to the principal surface of the wiring board, and configured to monitor a potential of a body. An end portion of the adhesion layer and an end portion of the base medium closer to the light receiving element are disposed such that the end portions do not overlap the light-receiving-element sealing portion when viewed from the direction normal to the principal surface of the wiring board.

In the biosensor according to the present invention, when a body, such as a fingertip, contacts the front surface of the plane electrode, light emitted from the light emitting element impinges on the body via the light-emitting-element sealing portion, the adhesion layer, and the base medium. Then, light passing through or reflected by the body is received by the light receiving element via the base medium, the adhesion layer, and the light-receiving-element sealing portion. With this operation, a photoplethysmographic signal indicating a pulse wave of the body is obtained. Simultaneously, the potential of the body which is in contact with the plane electrode is detected by the plane electrode.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. In the biosensor according to the present invention, the end portions of the base medium and the adhesion layer closer to the light receiving element are disposed such that they do not overlap the light-receiving-element sealing portion when viewed from the direction normal to the principal surface of the wiring board. Accordingly, it is less likely that stray light propagating through the base medium and the adhesion layer and exiting from the end portions of the base medium and the adhesion layer will impinge on the light-receiving-element sealing portion. It is thus possible to reduce the amount of stray light which does not pass through a body and which is received after passing through the base medium and the adhesion layer. As a result, in the biosensor which obtains a photoplethysmographic signal, it is possible to reduce the amount of stray light which is received without passing through a body.

In the biosensor according to the present invention, an end portion of the adhesion layer and an end portion of the base medium closer to the light emitting element may preferably be disposed such that the end portions do not overlap the light-emitting-element sealing portion when viewed from the direction normal to the principal surface of the wiring board.

With this configuration, it is less likely that light emitted from the light emitting element will impinge on the end portions of the base medium and the adhesion layer through the light-emitting-element sealing portion. It is thus possible to further reduce the amount of stray light which does not pass through a body and which is transmitted through the base medium and the adhesion layer.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion; and a plane electrode attached to a principal surface of the base medium such that the plane electrode overlaps neither of the light emitting element nor the light receiving element when viewed from a direction normal to the principal surface of the wiring board, and configured to monitor a potential of a body. An end portion of the adhesion layer and an end portion of the base medium closer to the light emitting element are disposed such that the end portions do not overlap the light-emitting-element sealing portion when viewed from the direction normal to the principal surface of the wiring board.

In the biosensor according to the present invention, when a body, such as a fingertip, contacts the front surface of the plane electrode, light emitted from the light emitting element impinges on the body via the light-emitting-element sealing portion, the adhesion layer, and the base medium. Then, light passing through or reflected by the body is received by the light receiving element via the base medium, the adhesion layer, and the light-receiving-element sealing portion. With this operation, a photoplethysmographic signal indicating a pulse wave of the body is obtained. Simultaneously, the potential of the body which is in contact with the plane electrode is detected by the plane electrode.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. In the biosensor according to the present invention, the end portions of the base medium and the adhesion layer closer to the light emitting element are disposed such that they do not overlap the light-emitting-element sealing portion when viewed from the direction normal to the principal surface of the wiring board. Accordingly, it is less likely that light emitted from the light emitting element will impinge on the end portions of the base medium and the adhesion layer through the light-emitting-element sealing portion. It is thus possible to further reduce the amount of stray light which does not pass through a body and which is transmitted through the base medium and the adhesion layer. As a result, in the biosensor which obtains a photoplethysmographic signal, it is possible to reduce the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; and a cover having light transmitting properties, disposed in parallel with the wiring board with the light shielding portion therebetween. An end portion of the cover closer to the light receiving element is disposed such that the end portion does not overlap the light-receiving-element sealing portion when viewed from a direction normal to the principal surface of the wiring board.

In the biosensor according to the present invention, when a body, such as a fingertip, contacts the front surface of the cover, light emitted from the light emitting element impinges on the body via the light-emitting-element sealing portion and the cover. Then, light passing through or reflected by the body is received by the light receiving element via the cover and the light-receiving-element sealing portion. With this operation, a photoplethysmographic signal indicating a pulse wave of the body is obtained. In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. In the biosensor according to the present invention, the end portion of the cover closer to the light receiving element is disposed such that it does not overlap the light-receiving-element sealing portion when viewed from the direction normal to the principal surface of the wiring board. Accordingly, it is less likely that stray light propagating through the cover and reflected by the end portion of the cover will impinge on the light-receiving-element sealing portion. It is thus possible to reduce the amount of stray light which does not pass through a body and which is received after passing through the cover. As a result, in the biosensor which obtains a photoplethysmographic signal, it is possible to reduce the amount of stray light which is received without passing through a body.

In the biosensor according to the present invention, an end portion of the cover closer to the light emitting element may preferably be disposed such that the end portion does not overlap the light-emitting-element sealing portion when viewed from the direction normal to the principal surface of the wiring board.

With this configuration, it is less likely that light emitted from the light emitting element will impinge on the end portion of the cover through the light-emitting-element sealing portion. It is thus possible to further reduce the amount of stray light which does not pass through a body and which is transmitted through the cover.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; and a cover having light transmitting properties, disposed in parallel with the wiring board with the light shielding portion therebetween. An end portion of the cover closer to the light emitting element is disposed such that the end portion does not overlap the light-emitting-element sealing portion when viewed from a direction normal to the principal surface of the wiring board.

In the biosensor according to the present invention, when a body, such as a fingertip, contacts the front surface of the cover, light emitted from the light emitting element impinges on the body via the light-emitting-element sealing portion and the cover. Then, light passing through or reflected by the body is received by the light receiving element via the cover and the light-receiving-element sealing portion. With this operation, a photoplethysmographic signal indicating a pulse wave of the body is obtained. In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. In the biosensor according to the present invention, the end portion of the cover closer to the light emitting element is disposed such that it does not overlap the light-emitting-element sealing portion when viewed from the direction normal to the principal surface of the wiring board. Accordingly, it is less likely that light emitted from the light emitting element will impinge on the end portion of the cover through the light-emitting-element sealing portion. It is thus possible to further reduce the amount of stray light which does not pass through a body and which is received after passing through the cover. As a result, in the biosensor which obtains a photoplethysmographic signal, it is possible to reduce the amount of stray light which is received without passing through a body.

In particular, in the biosensor according to the present invention, a lateral surface of the end portion of the cover closer to the light receiving element may preferably be disposed such that the lateral surface does not intersect with an imaginary line connecting a light receiving portion of the light receiving element and a peripheral portion of an opening of the light-receiving-element sealing portion.

With this configuration, it is even less likely that stray light reflected by the end portion of the cover will impinge on the light-receiving-element sealing portion. It is thus possible to more effectively reduce the amount of stray light which does not pass through a body and which is received after passing through the cover.

In the biosensor according to the present invention, a lateral surface of the end portion of the cover closer to the light emitting element may preferably be disposed such that the lateral surface does not intersect with an imaginary line connecting a light emitting portion of the light emitting element and a peripheral portion of an opening of the light-emitting-element sealing portion.

With this configuration, it is even less likely that light emitted from the light emitting element will impinge on the end portion of the cover through the light-emitting-element sealing portion. It is thus possible to more effectively reduce the amount of stray light which does not pass through a body and which is transmitted through the cover.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; and an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion. An end portion of the adhesion layer and an end portion of the base medium closer to the light receiving element are disposed such that the end portions do not overlap the light-receiving-element sealing portion when viewed from a direction normal to the principal surface of the wiring board.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. In the biosensor according to the present invention, the end portions of the base medium and the adhesion layer closer to the light receiving element are disposed such that they do not overlap the light-receiving-element sealing portion when viewed from the direction normal to the principal surface of the wiring board. Accordingly, it is less likely that stray light propagating through the base medium and the adhesion layer and exiting from the end portions of the base medium and the adhesion layer will impinge on the light-receiving-element sealing portion. It is thus possible to reduce the amount of stray light which does not pass through a body and which is received after passing through the base medium and the adhesion layer. As a result, in the biosensor which obtains a photoplethysmographic signal, it is possible to reduce the amount of stray light which is received without passing through a body.

A biosensor according to the present invention includes: a wiring board; a light emitting element and a light receiving element disposed on a principal surface of the wiring board with a predetermined spacing between the light emitting element and the light receiving element; a light-emitting-element sealing portion having light transmitting properties, disposed on the principal surface of the wiring board and configured to seal the light emitting element; a light-receiving-element sealing portion having light transmitting properties, disposed on the principal surface of the wiring board and configured to seal the light receiving element; a light shielding portion disposed between the light-emitting-element sealing portion and the light-receiving-element sealing portion; a base medium having light transmitting properties, disposed in parallel with the wiring board with the light shielding portion therebetween; and an adhesion layer having light transmitting properties, disposed between the base medium and the light shielding portion and/or the light-emitting-element sealing portion and the light-receiving-element sealing portion, and configured to bond the base medium with the light shielding portion and/or the light-emitting-element sealing portion and the light-receiving-element sealing portion. An end portion of the adhesion layer and an end portion of the base medium closer to the light emitting element are disposed such that the end portions do not overlap the light-emitting-element sealing portion when viewed from a direction normal to the principal surface of the wiring board.

In the biosensor according to the present invention, the light shielding portion is disposed between the light-emitting-element sealing portion and the light-receiving-element sealing portion. Accordingly, light emitted from the light emitting element is blocked from directly impinging on the light receiving element by the provision of the light shielding portion. In the biosensor according to the present invention, the end portions of the base medium and the adhesion layer closer to the light emitting element are disposed such that they do not overlap the light-emitting-element sealing portion when viewed from the direction normal to the principal surface of the wiring board. Accordingly, it is less likely that light emitted from the light emitting element will impinge on the end portions of the base medium and the adhesion layer through the light-emitting-element sealing portion. It is thus possible to further reduce the amount of stray light which does not pass through a body and which is transmitted through the base medium and the adhesion layer. As a result, in the biosensor which obtains a photoplethysmographic signal, it is possible to reduce the amount of stray light which is received without passing through a body.

According to the present invention, in a biosensor which obtains photoplethysmographic signals, it is possible to reduce the amount of stray light which is received without passing through a body.

DETAILED DESCRIPTION OF THE PREFERRED EMBODIMENTS

Figure 1:
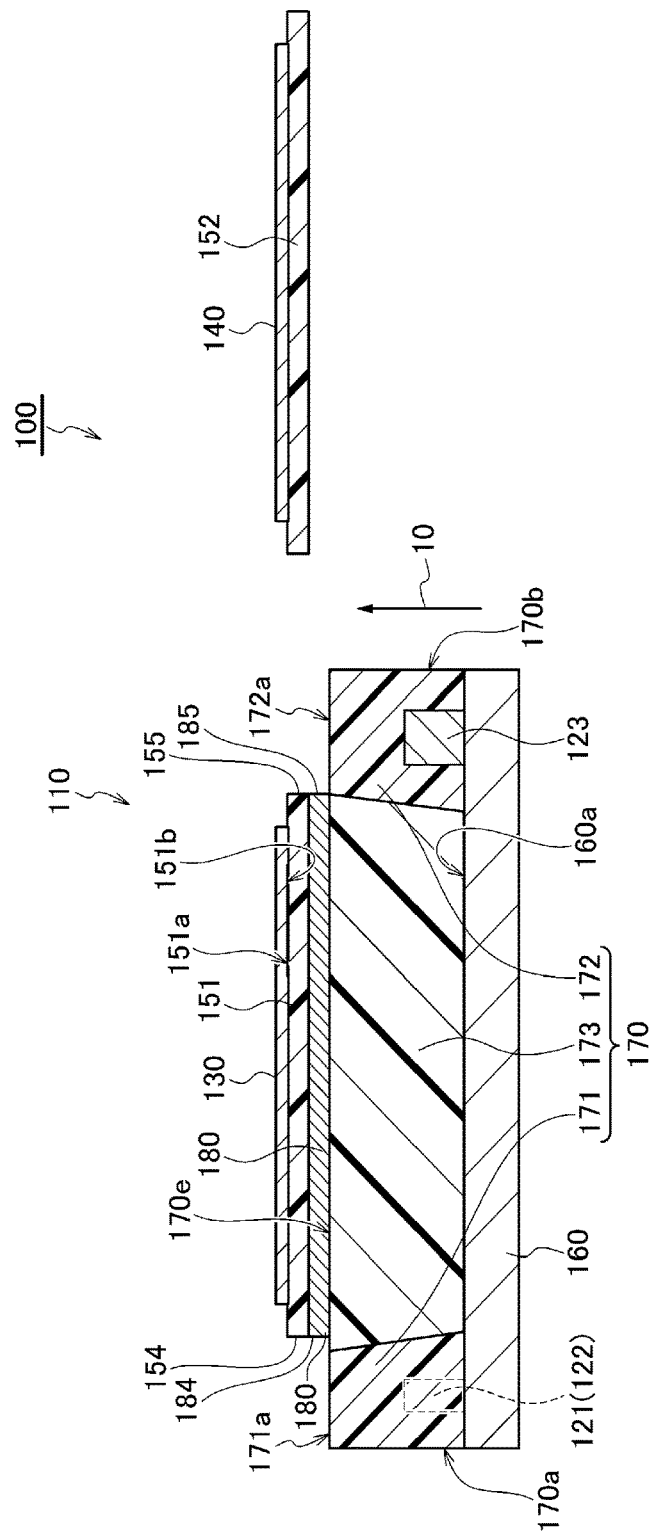
FIG. 1 is a longitudinal sectional view of a biosensor according to a first embodiment.

A preferred embodiment of the present invention will be described below with reference to the drawings. In the drawings, the same elements are designated by like reference numerals, and an explanation of the same element will be given only once.

First Embodiment

Figure 2:
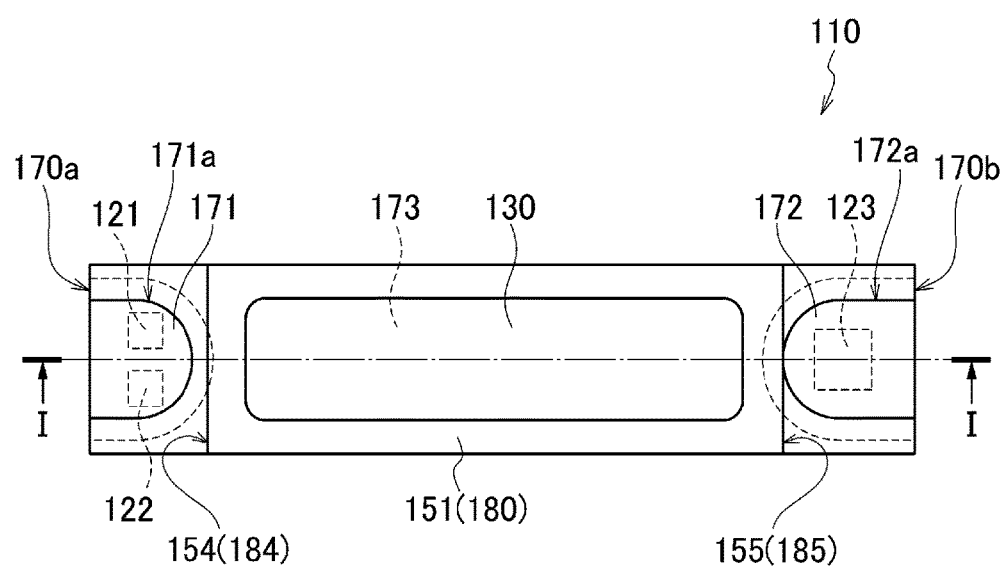
FIG. 2 is a plan view of a sensor unit forming the biosensor according to the first embodiment.
Figure 3:
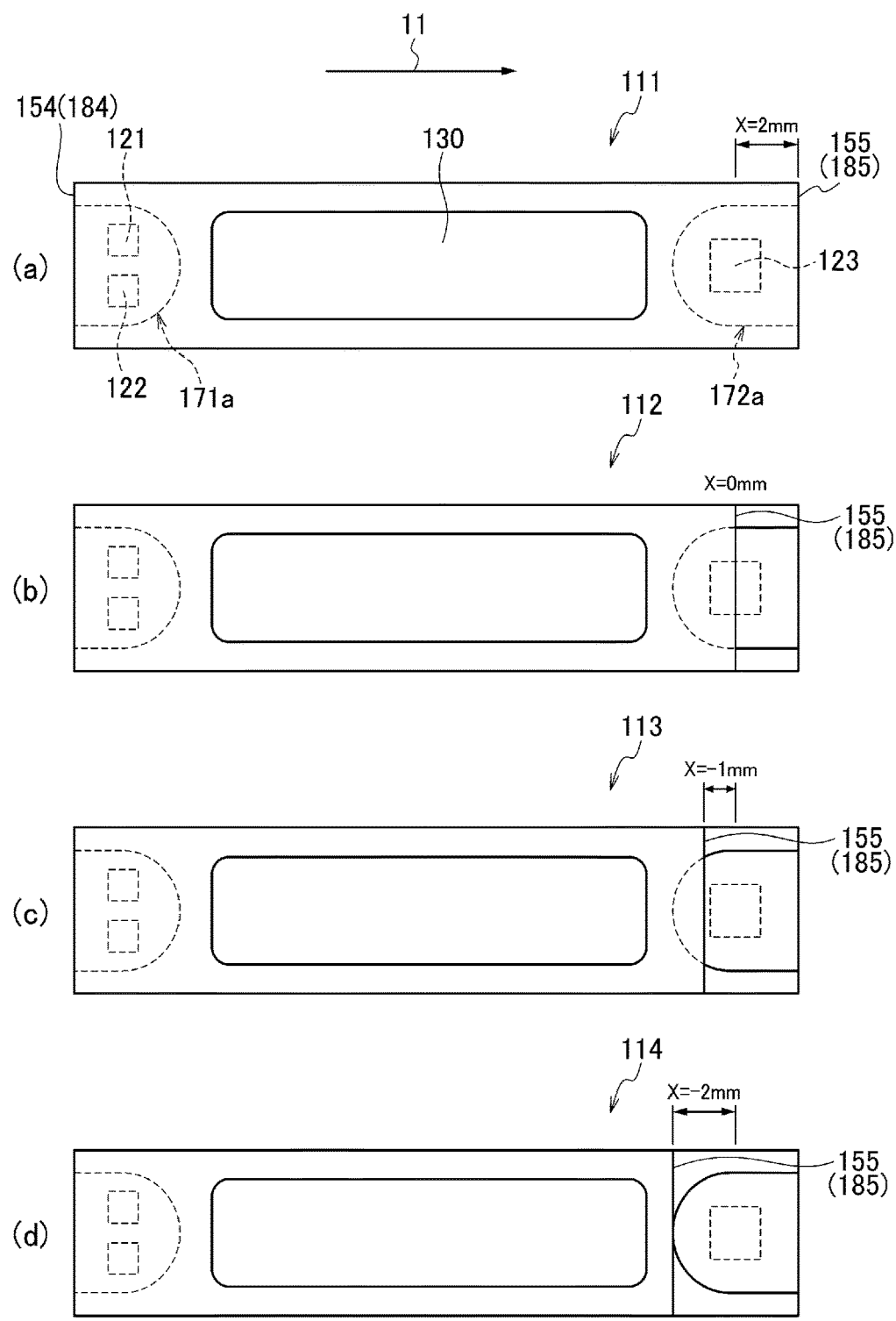
FIG. 3 shows plan views illustrating the configurations of sensor units of comparative examples.

The configuration of a biosensor 100 according to a first embodiment will be described below with reference to FIGS. 1 through 3. FIG. 1 is a longitudinal sectional view of the biosensor 100. FIG. 2 is a plan view of a sensor unit 110 forming the biosensor 100. In FIG. 1, a sectional view taken along line I-I in FIG. 2 is shown.

The biosensor 100 is a sensor which performs simultaneous detection (monitoring) of items of biological information upon a fingertip touching the biosensor 100, for example, taking of an electrocardiogram and measuring of the pulse and oxygen saturation are performed at the same time. The biosensor 100 optically measures the pulse and oxygen saturation by utilizing absorption characteristics of hemoglobin within the blood, and at the same time, it electrically monitors a change in the potential generated in accordance with the activity of the heart (takes an electrocardiogram) by using two electrodes 130 and 140.

The biosensor 100 includes two light emitting elements 121 and 122, a light receiving element 123, a first electrocardiograph electrode 130, a second electrocardiograph electrode 140, base mediums 151 and 152, a wiring board 160, a sealing section 170, and an adhesion layer 180.

The second electrocardiograph electrode 140 and the base medium 152 are integrally formed. The base medium 152 is formed in a rectangular shape, and the second electrocardiograph electrode 140 is disposed on the principal surface of the base medium 152. The second electrocardiograph electrode 140 is formed in a rectangular shape such that the contour of the rectangle is smaller than that of the base medium 152. The base medium 152 may be formed from a material, such as a resin. The base medium 152 does not have to have light transmitting properties.

The two light emitting elements 121 and 122, the light receiving element 123, the first electrocardiograph electrode 130, the base medium 151, the wiring board 160, the sealing section 170, and the adhesion layer 180 are integrally formed. Hereinafter, for the sake of convenience, this integrally formed unit will be referred to as the "sensor unit 110". This sensor unit 110 is formed generally in a rectangular parallelepiped. In FIG. 1, the height is shown in a relatively enlarged dimension for representation.

The light emitting elements 121 and 122 and the light receiving element 123 are mounted on a principal surface 160a of the wiring board 160 formed in a rectangular shape. The light emitting elements 121 and 122 are disposed side by side on a shorter side of the wiring board 160 at one end portion of the principal surface 160a. Meanwhile, the light receiving element 123 is disposed at the other end portion of the principal surface 160a. The distance from the light emitting elements 121 and 122 to the light receiving element 123 is set to be, for example, about 4 to 20 mm.

The two light emitting elements 121 and 122 emit light beams of different wavelengths in order to obtain the ratio of oxyhemoglobin to deoxyhemoglobin indicating oxygen saturation within the blood. For example, the light emitting element 121 emits light around an infrared light range in which the absorption coefficient of oxyhemoglobin is high. The light emitting element 122 emits light around a red light range in which the absorption coefficient of deoxyhemoglobin is high.

As the light emitting elements 121 and 122, LED, VCSEL, a resonator LED, or the like, may be used. As the light receiving element 123, a photodiode, a phototransistor, or the like, may be suitably used.

The sealing section 170 is formed in the shape of a rectangular parallelepiped on the principal surface 160a of the wiring board 160. The sealing section 170 includes a light-emitting-element sealing portion 171 for sealing the light emitting elements 121 and 122, a light-receiving-element sealing portion 172 for sealing the light receiving element 123, and a light shielding portion 173.

The light-emitting-element sealing portion 171 is formed from a translucent resin in a columnar shape of a generally elliptical arc in cross section and seals the light emitting elements 121 and 122. The light-emitting-element sealing portion 171 is exposed to a lateral surface 170a of the sealing section 170 on the side closer to the light emitting elements 121 and 122. The light-receiving-element sealing portion 172 is formed from a translucent resin in a columnar shape of a generally elliptical arc in cross section and seals the light receiving element 123. The light-receiving-element sealing portion 172 is exposed to a lateral surface 170b of the sealing section 170 on the side closer to the light receiving element 123. As the translucent resin forming the light-emitting-element sealing portion 171 and the light-receiving-element sealing portion 172, a transparent epoxy resin, for example, is used.

The light shielding portion 173 is formed by filling a resin having light-shielding properties into a region between the light-emitting-element sealing portion 171 and the light-receiving-element sealing portion 172 and into a peripheral region outside the light-emitting-element sealing portion 171 and the light-receiving-element sealing portion 172 on the principal surface 160a of the wiring board 160. As the light shielding portion 173, for example, an epoxy resin containing powder having light shielding properties, such as carbon black, is suitably used.

The top surfaces of the light-emitting-element sealing portion 171, the light-receiving-element sealing portion 172, and the light shielding portion 173 define a top surface 170e of the sealing section 170. The base medium 151 formed in a rectangular shape is bonded to the top surface 170e of the sealing section 170 with the adhesion layer 180 therebetween. A back surface 151b of the base medium 151 is bonded to the top surface 170e of the sealing section 170 in a state in which it opposes the principal surface 160a of the wiring board 160. The base medium 151 and the adhesion layer 180 are formed in the same shape and are disposed such that they overlap each other.

An end portion 184 of the adhesion layer 180 and an end portion 154 of the base medium 151 closer to the light emitting elements 121 and 122 are positioned such that they do not overlap an opening 171a of the light-emitting-element sealing portion 171 when viewed from a direction 10 normal to the principal surface 160a of the wiring board 160.

An end portion 185 of the adhesion layer 180 and an end portion 155 of the base medium 151 closer to the light receiving element 123 are positioned such that they do not overlap an opening 172a of the light-receiving-element sealing portion 172 when viewed from the direction 10 normal to the principal surface 160a.

The adhesion layer 180 may be formed from, for example, an acrylic resin. If the adhesion layer 180 overlaps neither of the opening 171a of the light-emitting-element sealing portion 171 nor the opening 172a of the light-receiving-element sealing portion 172, the base medium 151 and the adhesion layer 180 do not have to have light transmitting properties.

The first electrocardiograph electrode 130 is formed in the shape of a rectangular thin film and is disposed on a principal surface 151a of the base medium 151. The first electrocardiograph electrode 130 is disposed between the light emitting elements 121 and 122 and the light receiving element 123 when viewed from the direction 10 normal to the principal surface 160a of the wiring board 160. Moreover, the electrocardiograph electrode 130 is disposed at a position at which it overlaps neither of the light emitting elements 121 and 122 nor the light receiving element 123 and at a position at which it overlaps neither of the opening 171a nor the opening 172a when viewed from the direction 10 normal to the principal surface 160a.

Figure 4:
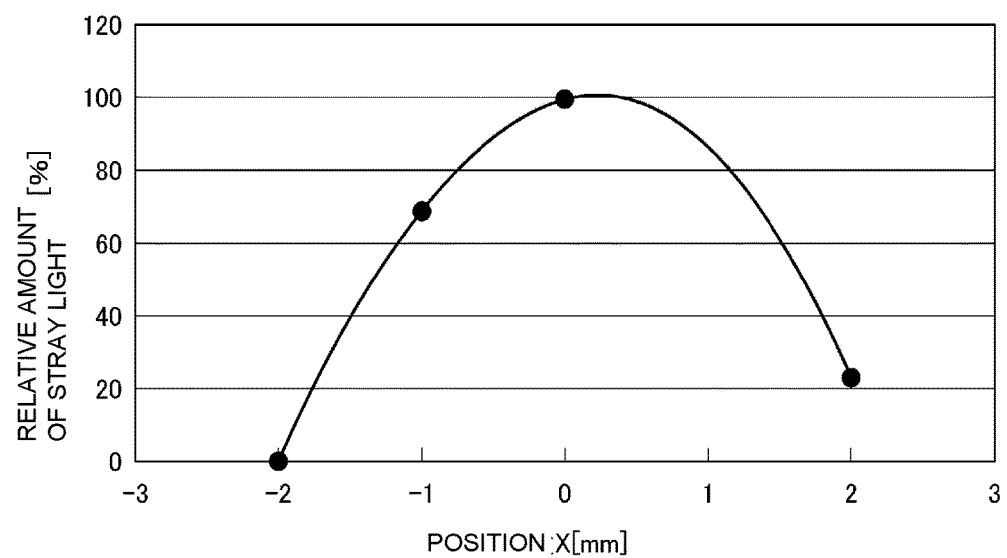
FIG. 4 is a graph illustrating the relationship between the amount of received stray light and the position of an end surface of a base medium with respect to a light receiving element.

A description will now be given, with reference to FIGS. 3 and 4, of the relationship between the amount of received stray light and the positions of the end portions 155 and 185 of the base medium 151 and the adhesion layer 180, respectively, with respect to the light receiving element 123 and the opening 172a. Parts (a) through (d) of FIG. 3 are plan views illustrating the configurations of sensor units 111 through 114 according to comparative examples. FIG. 4 is a graph illustrating the relationship between the amount of received stray light and the positions of the end portions 155 and 185 with respect to the position of the light receiving element 123.

In the sensor units 111 through 114, the end portion 154 of the base medium 151 and the end portion 184 of the adhesion layer 180 overlap each other. In the sensor units 111 through 114, the end portions 154 and 184 closer to the light emitting elements 121 and 122 are positioned such that they extend until the lateral surface 170a of the sealing portion 170.

In the sensor units 111 through 114, the end portion 155 of the base medium 151 and the end portion 185 of the adhesion layer 180 overlap each other. In the sensor units 111 through 114, the positions of the end portions 155 and 185 with respect to the light receiving element 123 and the opening 172a of one sensor are different from those of another sensor.

In the sensor unit 111, the positions of the end portions 155 and 185 coincide with the position of the lateral surface 170b of the sealing section 170. The end portions 155 and 185 of the sensor unit 111 are disposed such that a position X in a direction 11 with respect to the center of the light receiving element 123 is +2 mm from the end portions 155 and 185. The direction 11 is a direction in which the light emitting elements 121 and 122 are connected to the light receiving element 123. In FIG. 3, the direction from the center of the light receiving element 123 to the lateral surface 170b (right side in FIG. 3) is a positive direction.

In the sensor unit 112, the end portions 155 and 185 are positioned above the center of the light receiving element 123, and are disposed such that the position X is 0 mm. In the sensor unit 113, the end portions 155 and 185 are positioned toward the left side of FIG. 3 from the center of the light receiving element 123 and are disposed such that the position X is −1 mm. In the sensor unit 114, the end portions 155 and 185 are positioned toward the left side of FIG. 3 from the center of the light receiving element 123 and are disposed such that the position X is −2 mm.

FIG. 4 illustrates the relationship between the amount of received stray light and the positions of the end portions 155 and 185 with respect to the position of the light receiving element 123. In the graph of FIG. 4, the horizontal axis represents the position X (mm). The vertical axis represents the relative amount of stray light (%), which indicates the relative amounts of stray light of the above-described individual sensor units 111 through 114 when the amount of stray light of the sensor unit 112 (X=0 mm) is 100. The graph of FIG. 4 shows that, as the absolute value of the position X, that is, the distance from the light receiving element 123 to the end portions 155 and 185, is increased, the relative amount of stray light is decreased. Although the above-described distance of the sensor unit 111 is the same as that of the sensor unit 114, the relative amount of stray light of the sensor unit 114 is smaller than that of the sensor unit 111.

The reason for this is as follows. In the sensor unit 114, the end portions 155 and 185 of the base medium 151 and the adhesion layer 180, respectively, are disposed at positions at which they do not overlap the opening 172a of the light-receiving-element sealing portion 172. Accordingly, it is less likely that stray light which has propagated through the base medium 151 and the adhesion layer 180 and which has reached the end portions 155 and 185 will impinge on the light-receiving-element sealing portion 172.

In the biosensor 100 according to this embodiment, when a fingertip contacts the front surface of the first electrocardiograph electrode 130, light emitted from the light emitting elements 121 and 122 impinges on the fingertip via the light-emitting-element sealing portion 171. Then, light passing through the fingertip is received by the light receiving element 123 via the light-receiving-element sealing portion 172. With this operation, a photoplethysmographic signal indicating a pulse wave of the fingertip is obtained. Simultaneously, the potential of the fingertip which is in contact with the first electrocardiograph electrode 130 and the potential of a fingertip which is in contact with the second electrocardiograph electrode 140 are detected.

In the biosensor 100 according to this embodiment, the end portions 155 and 185 of the base medium 151 and the adhesion layer 180, respectively, closer to the light receiving element 123 are disposed such that they do not overlap the light-receiving-element sealing portion 172 when viewed from the direction 10 normal to the principal surface 160a of the wiring board 160. Accordingly, it is less likely that stray light propagating through the base medium 151 and the adhesion layer 180 and exiting from the end portions 155 and 185 of the base medium 151 and the adhesion layer 180, respectively, will impinge on the light-receiving-element sealing portion 172. It is thus possible to reduce the amount of stray light which does not pass through a body and which is received after passing through the base medium 151 and the adhesion layer 180.

Additionally, in the biosensor 100 according to this embodiment, the end portions 154 and 184 of the base medium 151 and the adhesion layer 180, respectively, closer to the light emitting elements 121 and 122 are disposed such that they do not overlap the light-emitting-element sealing portion 171 when viewed from the direction 10 normal to the principal surface 160a of the wiring board 160. Accordingly, it is less likely that light emitted from the light emitting elements 121 and 122 will impinge on the end portions 154 and 184 of the base medium 151 and the adhesion layer 180, respectively, through the light-emitting-element sealing portion 171. It is thus possible to further reduce the amount of stray light which does not pass through a body and which is transmitted through the base medium 151 and the adhesion layer 180.

As a result, in the biosensor 100 of this embodiment which simultaneously obtains a photoplethysmographic signal and potentials of a body (electrocardiogram), it is possible to reduce the amount of stray light which is received without passing through a body.

In this embodiment, photoelectric pulse waves and an electrocardiogram are obtained simultaneously. However, if an electrocardiogram is not obtained, that is, only photoelectric pulse waves are measured, the provision of the first and second electrocardiograph electrodes 130 and 140 is not necessary, and thus, the first and second electrocardiograph electrodes 130 and 140 may be omitted.

Second Embodiment

Figure 5:
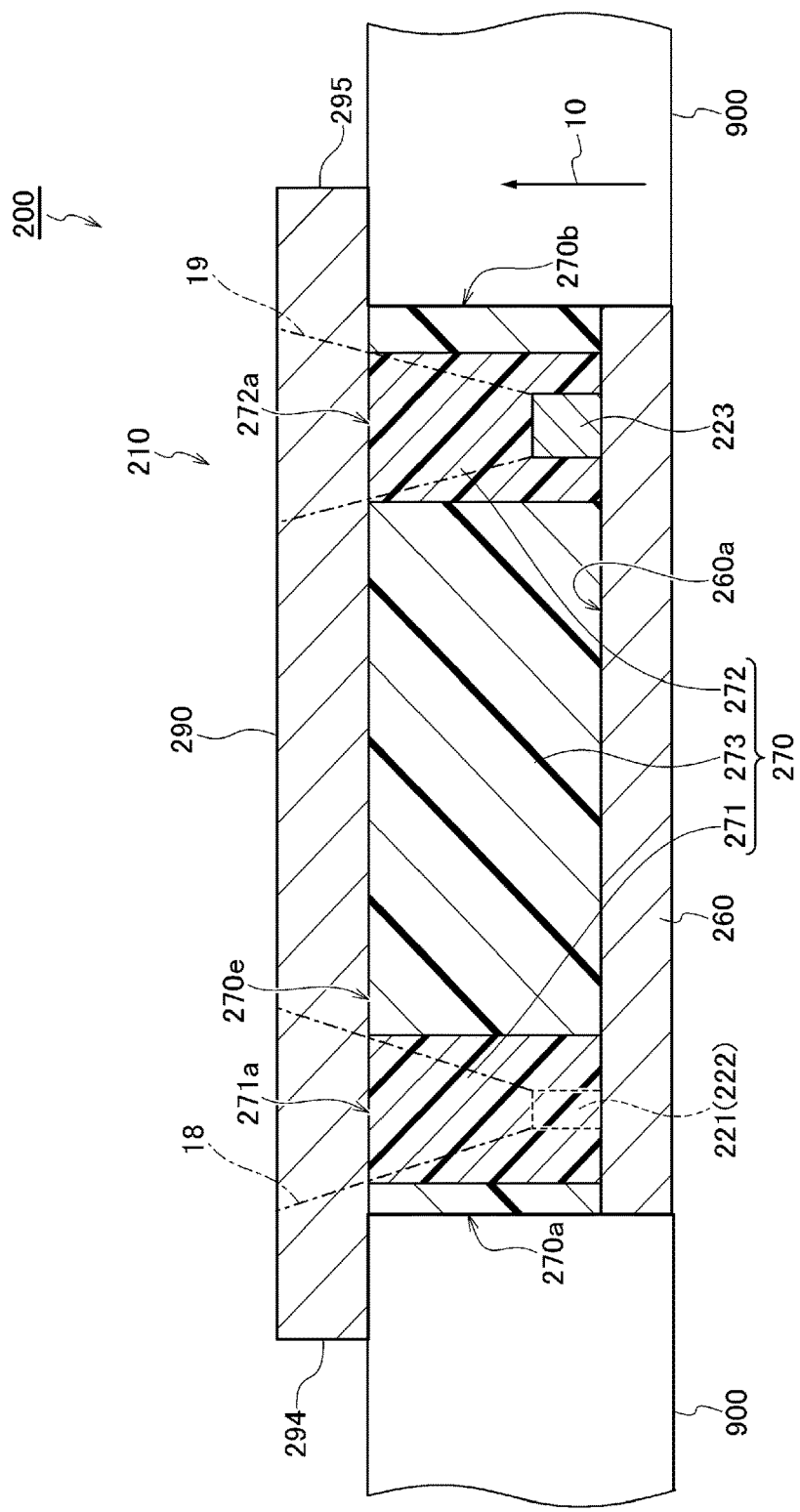
FIG. 5 is a longitudinal sectional view of a biosensor according to a second embodiment.

The configuration of a biosensor 200 according to a second embodiment will be described below with reference to FIG. 5. FIG. 5 is a longitudinal sectional view of the biosensor 200.

The biosensor 200 is a sensor which performs detection (monitoring) of biological information, for example, measuring of the pulse and oxygen saturation, upon a fingertip touching the biosensor 200. The biosensor 200 optically measures the pulse and oxygen saturation by utilizing absorption characteristics of hemoglobin within the blood.

In order to implement this function, the biosensor 200 includes two light emitting elements 221 and 222, a light receiving element 223, a wiring board 260, a sealing section 270, and a cover 290.

The wiring board 260 is formed in a rectangular sheet-like shape. On the wiring board 260, the light emitting elements 221 and 222, the light receiving element 223, the sealing section 270, and the cover 290 are integrally formed. Hereinafter, for the sake of convenience, this integrally formed unit will be referred to as the "sensor unit 210". This sensor unit 210 is formed generally in a rectangular parallelepiped. In FIG. 5, the height is shown in a relatively enlarged dimension for representation. The sensor unit 210 is attached to a casing 900 which is made from an opaque resin by means of, for example, the insertion of the sensor unit 210 into a rectangular hole formed in the casing 900. Alternatively, by using, for example, a sheet-like fixing member, the sensor unit 210 may be fixed by holding the sensor unit 210 from the rear surface of the wiring board 260.

The light emitting elements 221 and 222 and the light receiving element 223 are mounted on a principal surface 260a of the wiring board 260 formed in a rectangular shape. The light emitting elements 221 and 222 are disposed side by side on a shorter side of the wiring board 260 at one end portion of the principal surface 260a. Meanwhile, the light receiving element 223 is disposed at the other end portion of the principal surface 260a. The distance from the light emitting elements 221 and 222 to the light receiving element 223 is set to be, for example, about 4 to 20 mm.

The two light emitting elements 221 and 222 emit light beams of different wavelengths in order to obtain the ratio of oxyhemoglobin to deoxyhemoglobin indicating oxygen saturation within the blood. For example, the light emitting element 221 emits light around an infrared light range in which the absorption coefficient of oxyhemoglobin is high. The light emitting element 222 emits light around a red light range in which the absorption coefficient of deoxyhemoglobin is high.

As the light emitting elements 221 and 222, LED, VCSEL (Vertical Cavity Surface Emitting LASER), a resonator LED, or the like, may be used. As the light receiving element 223, a photodiode, a phototransistor, or the like, may be suitably used.

The sealing section 270 is formed in the shape of a rectangular parallelepiped on the principal surface 260a of the wiring board 260. The sealing section 270 includes a light-emitting-element sealing portion 271 for sealing the light emitting elements 221 and 222, a light-receiving-element sealing portion 272 for sealing the light receiving element 223, and a light shielding portion 273.

The light-emitting-element sealing portion 271 is formed from a translucent resin in a cylindrical shape and seals the light emitting elements 221 and 222. The light-receiving-element sealing portion 272 is formed from a translucent resin in a cylindrical shape and seals the light receiving element 223. As the translucent resin forming the light-emitting-element sealing portion 271 and the light-receiving-element sealing portion 272, a transparent epoxy resin, for example, is used.

The light shielding portion 273 is formed by filling a resin having light-shielding properties into a region between the light-emitting-element sealing portion 271 and the light-receiving-element sealing portion 272 and into a region around the light-emitting-element sealing portion 271 and the light-receiving-element sealing portion 272 on the principal surface 260a of the wiring board 260. The light shielding portion 273 defines four lateral surfaces of the sealing section 270. As the light shielding portion 273, for example, an epoxy resin containing powder having light shielding properties, such as carbon black, is suitably used.

The top surfaces of the above-described light-emitting-element sealing portion 271, light-receiving-element sealing portion 272, and light shielding portion 273 define a top surface 270e of the sealing section 270. The cover 290 having light transmitting properties is attached to the top surface 270e of the sealing section 270. That is, the cover 290 is disposed in parallel with the wiring board 260 via the sealing section 270 (light shielding portion 273). The cover 290 is a sheet-like member having a thickness of about 0.1 to 2 mm made from an acrylic, polycarbonate, or PET (polyethylene terephthalate) resin having translucent properties. The cover 290 is formed longer in the longitudinal direction and in the widthwise direction than the sealing section 270, and covers an opening 271a of the light-emitting-element sealing portion 271 and an opening 272a of the light-receiving-element sealing portion 272.

An end portion 294 of the cover 290 closer to the light emitting elements 221 and 222 is positioned farther outward than the opening 271a of the light-emitting-element sealing portion 271. That is, the end portion 294 of the cover 290 is disposed such that it does not overlap the opening 271a when viewed from the direction 10 normal to the principal surface 260a of the wiring board 260. More specifically, the cover 290 is disposed such that the lateral surface (end surface) of the end portion 294 of the cover 290 closer to the light emitting elements 221 and 222 does not intersect with an imaginary line 18 connecting the light emitting portion (or the light emitting surface) of each of the light emitting elements 221 and 222 and the peripheral portion of the opening 271a of the light-emitting-element sealing portion 271.

An end portion 295 of the cover 290 closer to the light receiving element 223 is positioned farther outward than the opening 272a of the light-receiving-element sealing portion 272. That is, the end portion 295 of the cover 290 is disposed such that it does not overlap the opening 272a when viewed from the direction 10 normal to the principal surface 260a. More specifically, the cover 290 is disposed such that the lateral surface (end surface) of the end portion 295 of the cover 290 closer to the light receiving element 223 does not intersect with an imaginary line 19 connecting the light receiving portion (or the light receiving surface) of the light receiving element 223 and the peripheral portion of the opening 272a of the light-receiving-element sealing portion 272.

The detection of biological information by using the biosensor 200 is performed by allowing a part of a body, for example, a fingertip of a left hand of a patient, to contact the biosensor 200.

When detecting biological information, light emitted from the light emitting elements 221 and 222 passes through the light-emitting-element sealing portion 271 and impinges on the cover 290 through the opening 271a. Light then passes through the cover 290 and impinges on the fingertip.

Light incident on and passing through the fingertip further passes through the cover 290 and impinges on the opening 272a of the light-receiving-element sealing portion 272. Then, light passes through the light-receiving-element sealing portion 272 and is received by the light receiving element 223. With this operation, a change in the intensity of light passing through the fingertip is obtained as a photoplethysmographic signal. In this case, since light beams of different wavelengths are emitted from the two light emitting elements 221 and 222, the intensity of the transmitted light concerning the two wavelengths can be obtained.

As discussed above in detail, according to this embodiment, when a fingertip contacts the front surface of the biosensor 200, light emitted from the light emitting elements 221 and 222 impinges on the fingertip via the light-emitting-element sealing portion 271 and the cover 290. Then, light passing through the fingertip is received by the light receiving element 223 via the cover 290 and the light-receiving-element sealing portion 272. With this operation, a photoplethysmographic signal indicating a pulse wave of the fingertip is obtained.

In the biosensor 200, the light shielding portion 273 is disposed between the light-emitting-element sealing portion 271 and the light-receiving-element sealing portion 272. Accordingly, light emitted from the light emitting elements 221 and 222 is blocked from directly impinging on the light receiving element 223 by the provision of the light shielding portion 273. Moreover, in the biosensor 200, the end portion 295 of the cover 290 closer to the light receiving element 223 is disposed such that it does not overlap the light-receiving-element sealing portion 272 when viewed from the direction normal to the principal surface 260a of the wiring board 260. Accordingly, it is less likely that stray light propagating through the cover 290 and reflected by the end portion 295 of the cover 290 will impinge on the light-receiving-element sealing portion 272. It is thus possible to reduce the amount of stray light which does not pass through a body and which is received through the cover 290. As a result, in the biosensor 200 which obtains a photoplethysmographic signal, it is possible to reduce the amount of stray light which is received without passing through a body.

In particular, in the biosensor 200, the cover 290 is disposed such that the lateral surface of the end portion 295 of the cover 290 closer to the light receiving element 223 does not intersect with the imaginary line 19 connecting the light receiving portion of the light receiving element 223 and the peripheral portion of the opening 272a of the light-receiving-element sealing portion 272. Accordingly, it is even less likely that stray light reflected by the end portion of the cover 290 will impinge on the light-receiving-element sealing portion 272. It is thus possible to more effectively reduce the amount of stray light which does not pass through a body and which is received through the cover 290.

In the biosensor 200, the end portion 294 of the cover 290 closer to the light emitting elements 221 and 222 is disposed such that it does not overlap the light-emitting-element sealing portion 271 when viewed from the direction normal to the principal surface 260a of the wiring board 260. Accordingly, it is less likely that light emitted from the light emitting elements 221 and 222 will impinge on the end portion of the cover 290 through the light-emitting-element sealing portion 271. It is thus possible to further reduce the amount of stray light which does not pass through a body and which is transmitted through the cover 290.

In particular, in the biosensor 200, the cover 290 is disposed such that the lateral surface (end surface) of the end portion 294 of the cover 290 closer to the light emitting elements 221 and 222 does not intersect with the imaginary line 18 connecting the light emitting portion of each of the light emitting elements 221 and 222 and the peripheral portion of the opening 271a of the light-emitting-element sealing portion 271. Accordingly, it is even less likely that light emitted from the light emitting elements 221 and 222 will impinge on the end portion 294 of the cover 290 through the light-emitting-element sealing portion 271. It is thus possible to more effectively reduce the amount of stray light which does not pass through a body and which is transmitted through the cover 290.

Modified Example

Figure 6:
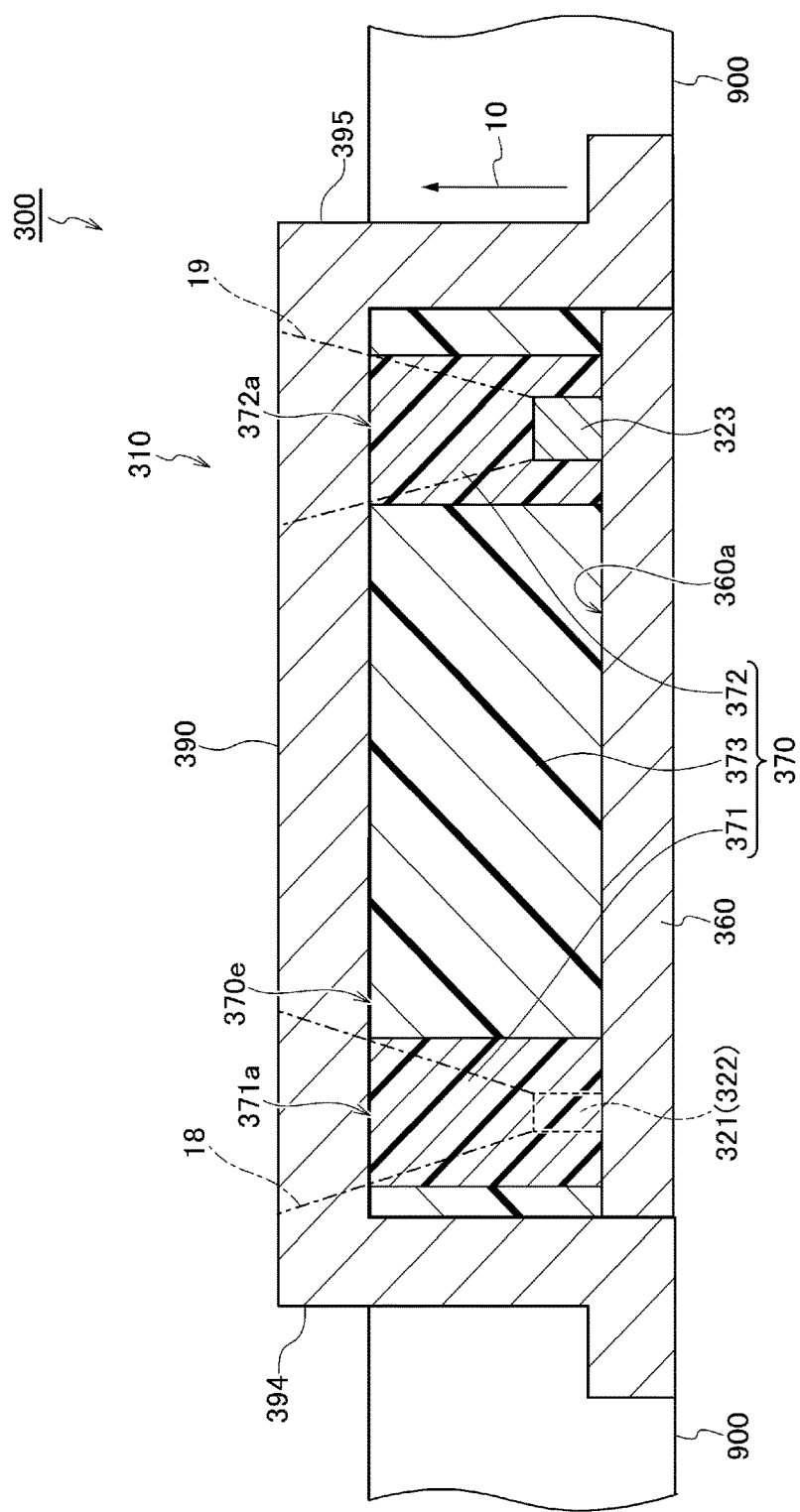
FIG. 6 is a longitudinal sectional view of a biosensor according to a modified example of the second embodiment.

In the second embodiment, the rectangular sheet-like cover 290 is used. Alternatively, as shown in FIG. 6, a cover 390 having a hat-like shape in cross section so as to cover a sealing section 370 may be used.

As in the above-described biosensor 200, in this modified example, the cover 390 is disposed such that the lateral surface (end surface) of an end portion 394 of the cover 390 closer to light emitting elements 321 and 322 does not intersect with the imaginary line 18 connecting the light emitting portion (or the light emitting surface) of each of the light emitting elements 321 and 322 and the peripheral portion of an opening 371a of a light-emitting-element sealing portion 371. The cover 390 is also disposed such that the lateral surface (end surface) of an end portion 395 of the cover 390 closer to a light receiving element 323 does not intersect with the imaginary line 19 connecting the light receiving portion (or the light receiving surface) of the light receiving element 323 and the peripheral portion of an opening 372a of a light-receiving-element sealing portion 372.

In this mode, advantages comparable to those achieved by the above-described biosensor 200 can be obtained. In this case, the cover 390 does not have to have a flange. That is, the cover 390 may be formed in the shape of an inverted U shape in cross section having an opening facing downward.

The embodiments of the present invention have been discussed. However, the present invention is not restricted to the above-described embodiments, and various modifications may be made. For example, in the first embodiment, the end portions 154 and 184 of the base medium 151 and the adhesion layer 180, respectively, are disposed farther inward than the opening 171a so that they may not overlap the opening 171a, and the end portions 155 and 185 of the base medium 151 and the adhesion layer 180, respectively, are disposed farther inward than the opening 172a so that they may not overlap the opening 172a. Alternatively, a light shielding portion may be formed around the light-emitting-element sealing portion 171 and around the light-receiving-element sealing portion 172 (see the above-described second embodiment), and the end portions 154 and 155 of the base medium 151 and the end portions 184 and 185 of the adhesion layer 180 may be disposed on the light shielding portion formed as described above.

In the first embodiment, the adhesion layer 180 without a core member is used. Alternatively, double-sided tape including a core member made from polyimide or PET and adhesive layers formed on both sides of the core member may be used.

Moreover, in the above-described embodiments, two light emitting elements are provided. However, the number of light emitting elements is not restricted to two, and one light emitting element may be provided, or three or more light emitting elements may be provided.

REFERENCE SIGNS LIST 100, 200, 300 biosensor
110, 210, 310 sensor unit
121, 122, 221, 222, 321, 322 light receiving element
123, 223, 323 light emitting element
130 first electrocardiograph electrode
140 second electrocardiograph electrode
150 base medium
160, 260, 360 wiring board
170, 270, 370 sealing section
171, 271, 371 light-emitting-element sealing portion
172, 272, 372 light-receiving-element sealing portion
173, 273, 373 light shielding portion
180 adhesion layer
290, 390 cover
10 normal direction
18, 19 imaginary line

The invention claimed is:
1. A biosensor comprising:
a wiring board having a principal surface;
a light emitting element and a light receiving element disposed on the principal surface of the wiring board;
a light-emitting-element sealer disposed on the principal surface of the wiring board to seal the light emitting element;
a light-receiving-element sealer disposed on the principal surface of the wiring board to seal the light receiving element;
a light shielding portion disposed between the light-emitting-element sealer and the light-receiving-element sealer;
a base medium with light transmitting properties disposed above the wiring board with the light shielding portion therebetween;
an adhesion layer with light transmitting properties disposed on at least one of the light shielding portion, the light-emitting-element sealer and the light-receiving- element sealer, wherein the adhesion layer bonds the base medium to the at least one of the light shielding portion, the light-emitting-element sealer portion and the light-receiving-element sealer; and a plane electrode disposed on the base medium, wherein the plane electrode does not intersect either a line extending in a direction normal to the principal surface of the wiring board and through the light emitting element or a line extending in the direction normal to the principal surface of the wiring board and through the light receiving element, wherein end portions of the adhesion layer and end portions of the base medium each do not overlap the light-receiving-element sealer, when viewed from the direction normal to the principal surface of the wiring board, or the end portions of the adhesion layer and end portions of the base medium each do not overlap the light-emitting-element sealer, when viewed from the direction normal to the principal surface of the wiring board.

2. The biosensor according to claim 1, wherein the plane electrode is configured to monitor a potential of a body.

3. The biosensor according to claim 1, wherein the plane electrode extends a length on the base medium such that the plane electrode is between the light emitting element and the light receiving element when viewed from the direction normal to the principal surface of the wiring board.

4. The biosensor according to claim 1, wherein the adhesion layer and the base medium do not overlap both the light-emitting-element sealer and the light-receiving-element sealer when viewed from the direction normal to the principal surface of the wiring board.

5. The biosensor according to claim 1, wherein the light emitting element comprises a pair of light emitting devices configured to emit light beams at different wavelengths.

6. The biosensor according to claim 5, wherein the pair of light emitting devices emit light in an infrared light range and a red light range, respectively.

7. The biosensor according to claim 1, wherein the light shielding portion comprises a rectangular parallelepiped shape on the principal surface of the wiring board.

8. The biosensor according to claim 1,
wherein a first end portion of the adhesion layer coincides with a lateral surface of the light-emitting-element sealer, and
wherein a second end portion of the adhesion layer coincides with a lateral surface of the light-receiving-element sealer.

9. The biosensor according to claim 1,
wherein a first end portion of the adhesion layer coincides with a lateral surface of the light-emitting-element sealer, and
wherein a second end portion of the adhesion layer overlaps the light receiving element when viewed from the direction normal to the principal surface of the wiring board.

10. The biosensor according to claim 9, wherein the second end portion of the adhesion layer overlaps a centerline of the light receiving element when viewed from the direction normal to the principal surface of the wiring board.

11. The biosensor according to claim 1, wherein a distance from the light emitting element to the light receiving element is between 4 mm and 20 mm.

12. A biosensor comprising:
a wiring board having a principal surface;
a light emitting element and a light receiving element disposed on the principal surface of the wiring board;
a light-emitting-element sealer having light transmitting properties and disposed on the principal surface of the wiring board to seal the light emitting element;
a light-receiving-element sealer having light transmitting properties and disposed on the principal surface of the wiring board to seal the light receiving element;
a light shielding portion disposed between the light-emitting-element sealer and the light-receiving-element sealer; and
a cover with light transmitting properties disposed in parallel with the wiring board with the light shielding portion therebetween,
wherein the cover is disposed such that end portions of the cover do not intersect a line extending in a direction normal to the principal surface of the wiring board and through the light emitting element or the end portions of the cover do not intersect a line extending in the direction normal to the principal surface of the wiring board and through the light receiving element.

13. The biosensor according to claim 12, wherein the cover comprises a first end portion adjacent to the light receiving element and a second end portion adjacent to the light emitting element.

14. The biosensor according to claim 13, wherein a lateral surface of the first end portion of the cover does not intersect a line extending in a direction from a light receiving portion of the light receiving element through a peripheral portion of an opening of the light-receiving-element sealer.

15. The biosensor according to claim 13, wherein a lateral surface of the second end portion of the cover does not intersect a line extending in a direction from a light emitting portion of the light emitting element through a peripheral portion of an opening of the light-emitting-element sealer.

16. The biosensor according to claim 12, wherein the light emitting element comprises a pair of light emitting devices configured to emit light beams at different wavelengths.

17. The biosensor according to claim 16, wherein the pair of light emitting devices emit light in an infrared light range and a red light range, respectively.

18. The biosensor according to claim 12, wherein the cover comprises an inverted U shape cross section having an opening facing downward.

19. A biosensor comprising:
a wiring board having a principal surface;
a light emitting element and a light receiving element disposed on the principal surface of the wiring board;
a light-emitting-element sealer disposed on the principal surface of the wiring board to seal the light emitting element;
a light-receiving-element sealer disposed on the principal surface of the wiring board to seal the light receiving element;
a light shielding portion disposed between the light-emitting-element sealer and the light-receiving-element sealer;
a base medium with light transmitting properties disposed above the wiring board with the light shielding portion therebetween; and
an adhesion layer with light transmitting properties disposed on at least one of the light shielding portion, the light-emitting-element sealer and the light-receiving-element sealer, wherein the adhesion layer bonds the base medium to the at least one of the light shielding portion, the light-emitting-element sealer portion and the light-receiving-element sealer,
wherein respective end portions of the adhesion layer and end portions of the base medium each closer to the light receiving element do not overlap the light-receiving-element sealer, when viewed from a direction normal to the principal surface of the wiring board.

20. A biosensor comprising:
a wiring board having a principal surface;
a light emitting element and a light receiving element disposed on the principal surface of the wiring board;
a light-emitting-element sealer disposed on the principal surface of the wiring board to seal the light emitting element;
a light-receiving-element sealer disposed on the principal surface of the wiring board to seal the light receiving element;
a light shielding portion disposed between the light-emitting-element sealer and the light-receiving-element sealer;
a base medium with light transmitting properties disposed above the wiring board with the light shielding portion therebetween; and
an adhesion layer with light transmitting properties disposed on at least one of the light shielding portion, the light-emitting-element sealer and the light-receiving-element sealer, wherein the adhesion layer bonds the base medium to the at least one of the light shielding portion, the light-emitting-element sealer portion and the light-receiving-element sealer,
wherein respective end portions of the adhesion layer and end portions of the base medium each closer to the light emitting element do not overlap the light-emitting-element sealer, when viewed from a direction normal to the principal surface of the wiring board.

* * * * *